US012083537B1

(12) United States Patent
Gold et al.

(10) Patent No.: US 12,083,537 B1
(45) Date of Patent: Sep. 10, 2024

(54) ION DISPERSING APPARATUS

(71) Applicants: Gil Gold, Kibutz Shalavin (IL); Tamir Levy, Efrat (IL)

(72) Inventors: Gil Gold, Kibutz Shalavin (IL); Tamir Levy, Efrat (IL)

( * ) Notice: Subject to any disclaimer, the term of this patent is extended or adjusted under 35 U.S.C. 154(b) by 393 days.

(21) Appl. No.: 17/672,996

(22) Filed: Feb. 16, 2022

Related U.S. Application Data

(60) Provisional application No. 63/152,390, filed on Feb. 23, 2021.

(51) Int. Cl.
*B03C 3/82* (2006.01)
*B03C 3/04* (2006.01)
*B03C 3/36* (2006.01)
*B03C 3/38* (2006.01)

(52) U.S. Cl.
CPC .................. *B03C 3/38* (2013.01); *B03C 3/04* (2013.01); *B03C 3/368* (2013.01); *B03C 3/82* (2013.01)

(58) Field of Classification Search
CPC ............. B03C 3/38; B03C 3/04; B03C 3/368; B03C 3/82
USPC ................................................ 95/15, 16, 60
See application file for complete search history.

(56) References Cited

U.S. PATENT DOCUMENTS

2006/0201119 A1* 9/2006 Song .................... B01D 53/007 55/471
2021/0402413 A1* 12/2021 Kim .......................... B03C 3/41
2022/0193694 A1* 6/2022 DiCarlo .................... B03C 3/45
2023/0249196 A1* 8/2023 Cao ........................... B03C 3/68 96/15
2023/0256375 A1* 8/2023 Lee ........................... B03C 3/78 96/52

OTHER PUBLICATIONS

Sterionizer Bipolar Ion Technology brochure.

* cited by examiner

*Primary Examiner* — Frank M Lawrence, Jr.
(74) *Attorney, Agent, or Firm* — Aronberg Goldgehn Davis & Garmisa

(57) ABSTRACT

The present disclosure generally relates to an ion dispersing apparatus. The apparatus is made a housing that accommodates a fan and an ion generator. Air is sucked into the housing at the bottom and exhausted out of the top by the fan. The ion generator sits above the fan and deposits ions into the system. Thus, when the fan generates airflow, the ions are deposited into the airflow and exhausted from the system without having to pass through the fan blades.

12 Claims, 4 Drawing Sheets

ION DISPERSING APPARATUS

BACKGROUND OF THE INVENTION

There are a number of ion dispersing systems on the market. For example, Filt Air Ltd. sells air filtration and purification systems using ion generators. In the Filt Air Ltd. systems, air flows over an ionizer in, for example, and HVAC unit.

Some of the problems that arise with the use of such systems is that the ions do not disperse fast enough. When the ions are released in a closed system, such as within an air duct, the charged particles are constrained and have a tendency to lose their charge or attach to other molecules shortly after being released by the ionizer. Thus, the ions are not able to disperse adequately into the atmosphere within the large air circulation system. As a result, only the air being forced through the system, such as the air within the HVAC unit, is subject to treatment with the ions before being dispersed into the room.

SUMMARY OF THE INVENTION

The present system generally relates to a device that generates and disperses ions uniformly into the atmosphere to treat air directly within the living space. The ion dispensing apparatus is equipped with a power supply, such as a battery, that powers a fan and an ion generator (also referred to as an ionizer). The fan draws air into the base of the apparatus, and generates an outflow of air in a pattern within the room itself. The ionizer is located proximal to the fan and releases ions into the outflow. The outflow is forced up through the top of the apparatus. The top is equipped with a substantially cone shaped duct that is positioned in close proximity (such as 3-15 cm) to both the fan and the ionizer. As the fan forces the outflow into the top, the cone disperses the outflow, and by extension the ions within the outflow, into the atmosphere in a substantially uniform 360 degree plume of air and ions. By maintaining close proximity among the top cone, ionizer, and fan, the system is able to quickly eject ions into the atmosphere before a majority of the ions are able to lose charge or connect with other molecules. Thus, the system is able to eject and disperse a substantially uniform flow of ions into a volume of gas (i.e. a room such as an office, restaurant, café, classroom, hotel room, etc.) such that the ions remain charged and active to clean the large volume of air by dispersing throughout the large volume.

DETAILED DESCRIPTION OF PREFERRED EMBODIMENTS

Figure 1:
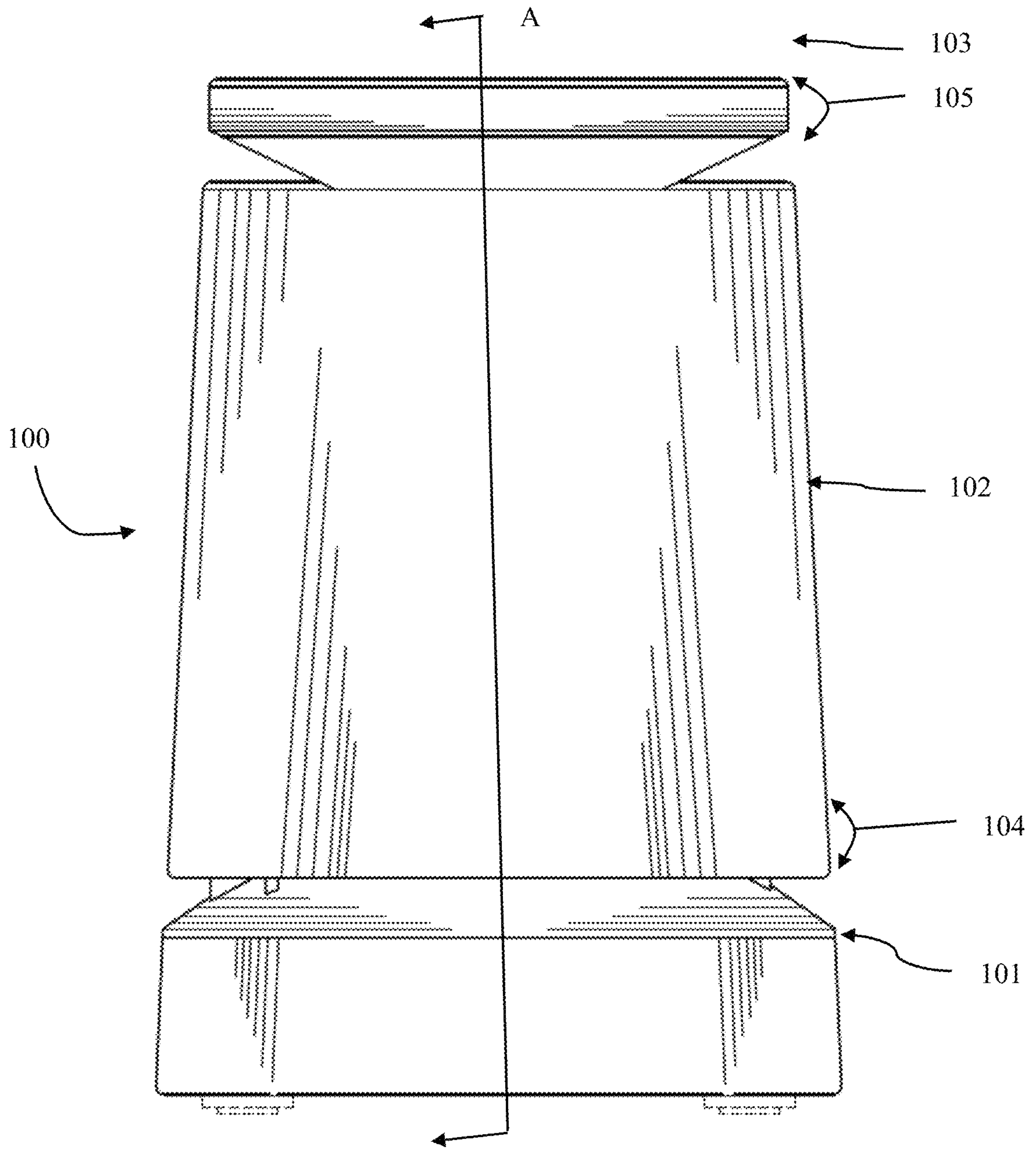
FIG. 1 is a side plan view of one embodiment of an ion dispersing apparatus.

The preferred embodiments of the present invention are described with reference to the drawings below. In the drawings, like numbers are used to refer to like elements. Unless otherwise stated, "and" is conjunctive, while or is disjunctive and conjunctive such that the condition "A or B" is satisfied by any of "A" alone, "B" alone, and "A and B" together.

Figure 2:
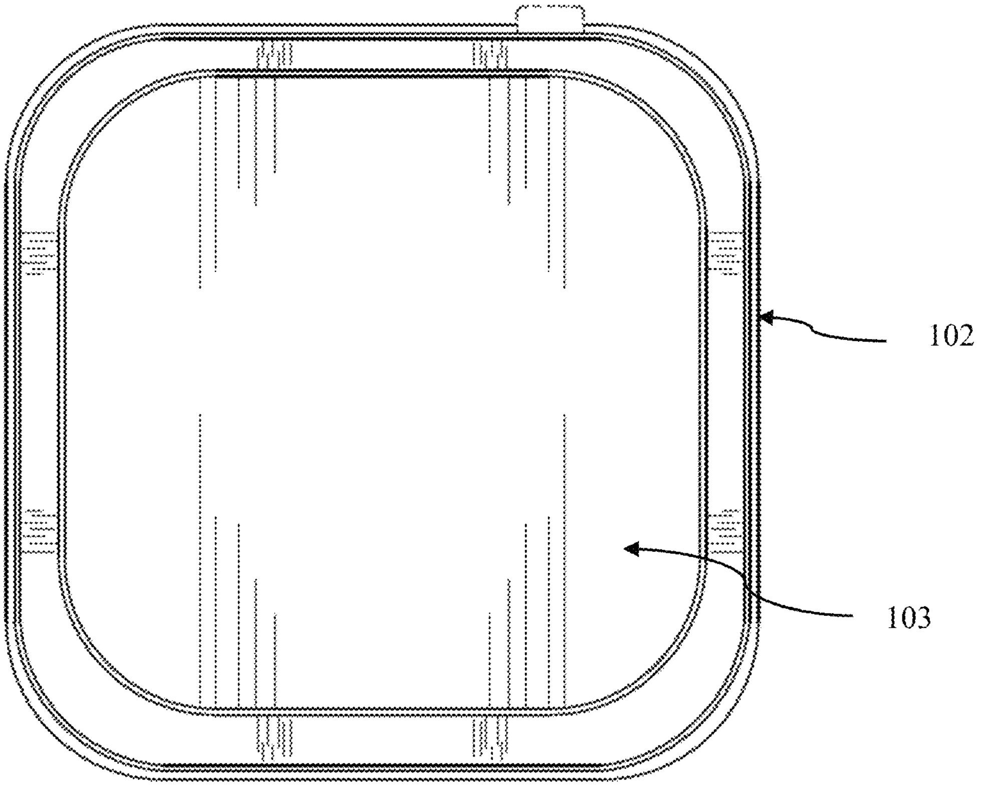
FIG. 2 is a top down view of one embodiment of an ion dispersing apparatus.
Figure 3:
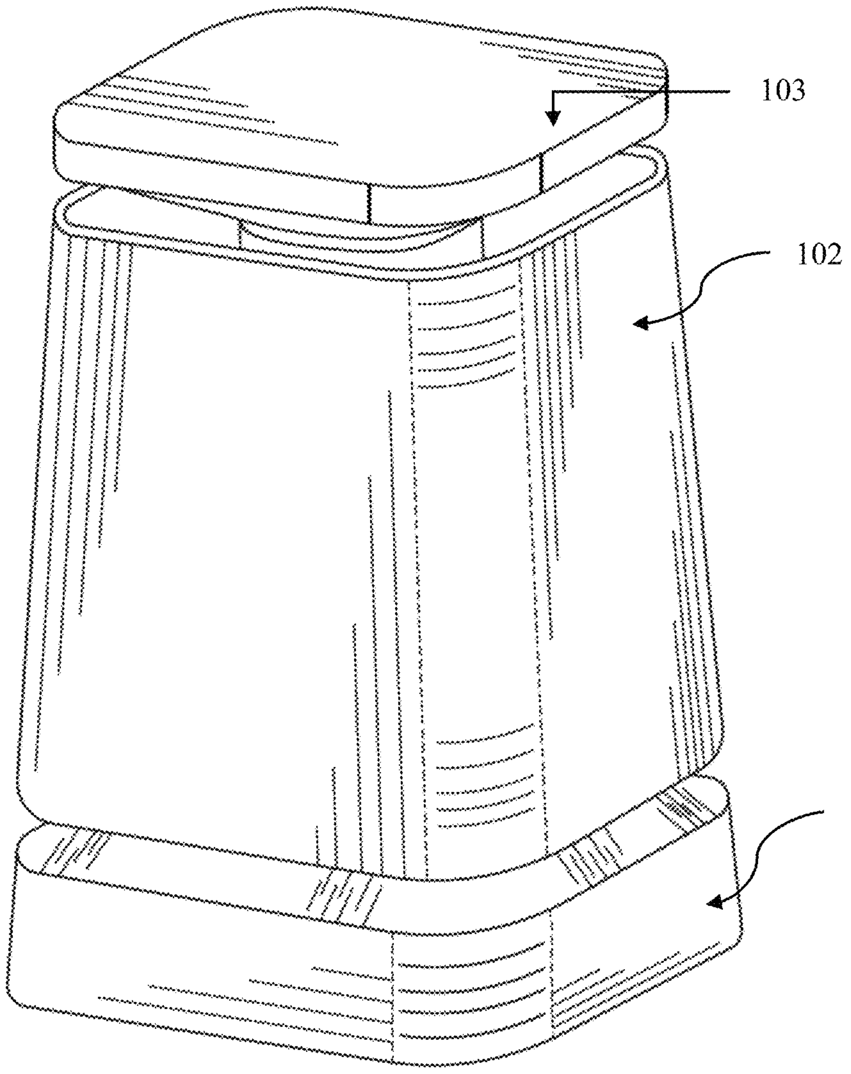
FIG. 3 is a perspective view of one embodiment of an ion dispersing apparatus.

Referring to FIGS. 1-3, the ion dispensing system 100 is formed of a base 101, a cowling 102, and a top 103. Between the base and the cowling and about the circumference of the dispensing system is an air intake gap 104. The gap allows airflow to enter the interior of the system about the entirety of the circumference of the system. There is also an air outflow gap 105 between the cowling and the top. The air outflow gap is formed about the entire circumference of the dispensing system so as to allow outflow of air about the entirety of the circumference of the system. The cowling separates the air intake gap from the air outflow gap.

Figure 4:
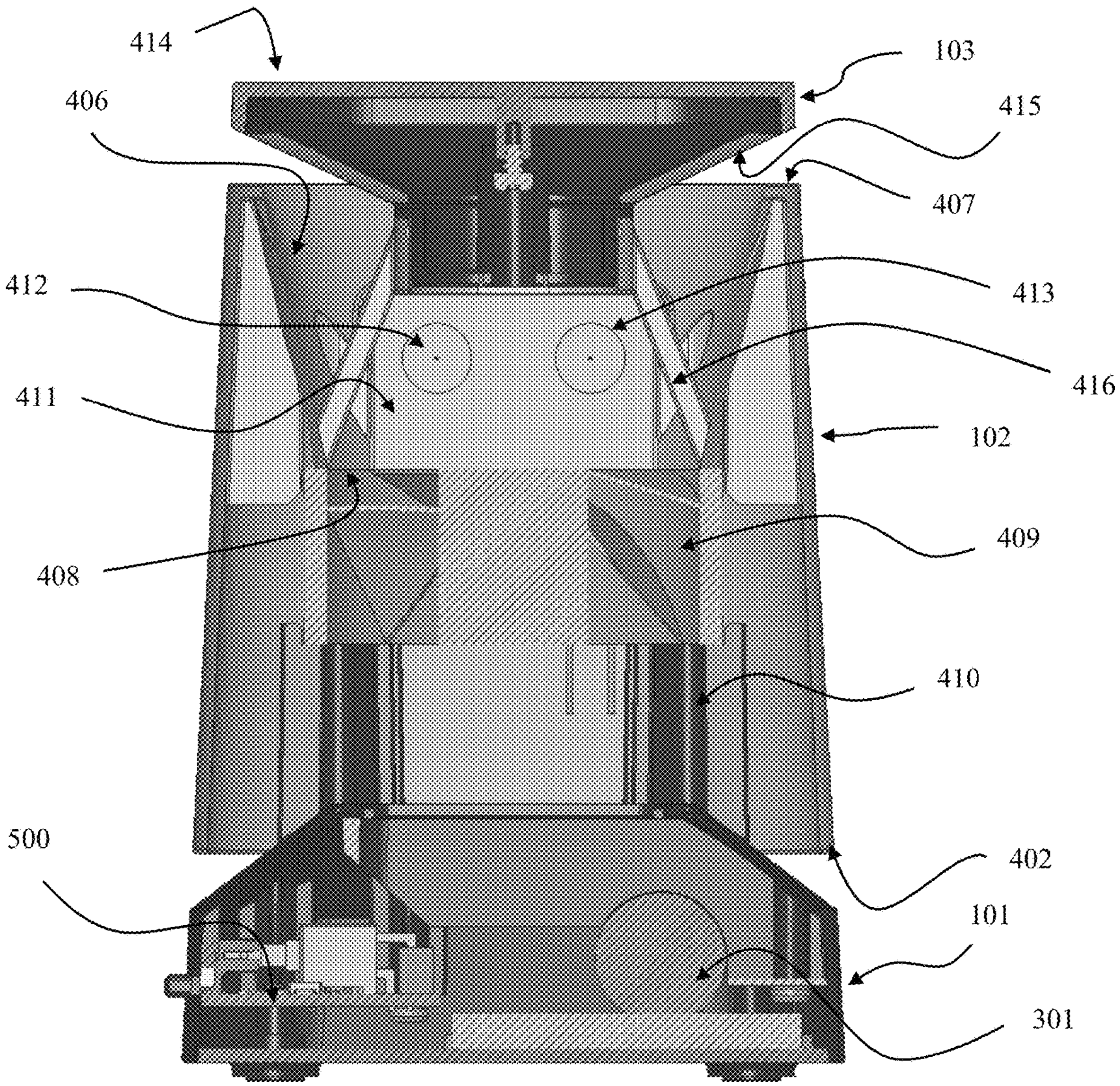
FIG. 4 is a cross-sectional view along line A of FIG. 1.

FIG. 4 is a cross-sectional view of the dispensing system about cross-sectional line A of FIG. 1. The cowling 102 includes an outer shell 402, and an inner cone 406. The inner cone is inverted at the upper section of the cowling such that the base of the cone mates with the upper rim 407 of the cowling and extends downward, tapering toward a central axis of the dispensing system. As used herein, the term "cone" is meant to encompass anything of a conical or pyramidal shape, including frustums. Thus, the inner cone 406 need not terminate in a point, but instead may have the shape of a frustum. The outer shell may be conical, but may alternatively be cylindrical or box like. The inner cone terminates at a mouth 408. The inner cone and outer shell are formed uniformly such that air entering at the gap 104 cannot exit the cowling at the rim 407, but rather must pass through the mouth 408. As shown in FIG. 1, the top, cowling and base may be symmetrical about a vertically oriented plane formed on a central vertical axis of the apparatus. The symmetry of the system helps create uniform airflow. The conical shape, with the base gap being larger than the top gap, enables a high volume of air to be sucked into the fan, concentrated, and then expelled at a higher pressure out of the smaller top gap, thereby enhancing the expulsion of ions into the atmosphere.

The cowling is affixed to a fan 409 that covers the mouth. The fan draws air in through gap 104 and expels air out of the cowling, through the mouth and out of gap 105. The fan is supported by one or more base legs 410. The legs connect to the base 101 and separate the intake of the fan from the base to promote air flow. The legs also raise the height of the fan up such that it is positioned within the cowling and separated from the gap 104. The separation helps draw air into the interior of the cowling uniformly about the circumference of the base.

The base also includes a conical upper portion that angles in to the interior of the cowling at the gap 104. The conical structure allows the system to maintain a relatively small distance between the bottom edge 402 of the cowling and the base 101 but still provide for substantial airflow into the interior of the cavity. The conical shape of the base angles up, toward the intake of the fan so as to direct air flowing through gap 104 up and toward the fan. As shown in the Figures, the top gap 105 is formed circumferentially around the rim 407 of the inner cone and between the top, and the bottom gap is formed circumferentially around bottom of the cowling and between the base and the cowling such that the top gap and bottom gap are each entirely open. By being entirely open, there is no structure between either the top and the rim, or the base and the bottom of the cowling that could impede the flow of air through either gap. For example, as shown in FIG. 4, beams 416 are position within the cavity formed by the sidewall of the inner cone, and not in the gap between the rim and the top. Similarly, support legs 410 are formed within the cavity formed by the outer shell and not within the gap between the outer shell and the base. Thus, air flows freely about the entirety of the circumference of the cowling at both the top gap and bottom gap as each gap is entirely open.

Within the interior of the base is a cavity that houses a control board 500 and a power supply. The power supply may be a battery. Alternatively it may be a power converter for accommodating power incoming from a traditional wall outlet. The control board allocates power to the fan and the ion generator.

The ion generator 411 includes ion depositors that are located above the fan and within the interior of the inner cone 406. In the embodiment shown, the ion generator has two ion depositors 412, 413 capable of generating and dispensing either or both positive and negative ions. While more or less could be used, it is important that the ion generators are positioned on the exhaust side of the fan, within the inner cone 406. The ion generators are further positioned proximal to the fan. In one embodiment, the ion depositors of the ion generator are positioned between 1-3 inches, vertically, from the fan and 0-0.5 inches horizontally from the fan. That positioning ensures that ions are deposited directly into exhaust path of the fan at a point where there is sufficient air flow to expel the ions and allow the ions to be guided into the airflow rather than clinging to the fan housing.

The top is provided with an upper platform, 414, and an inverted conical bottom 415. The conical bottom extends from an outer edge of the top down and inward, into the volume of the inner cone 406 of the cowling. The top is supported by one of more beams 416. The beams hold the top such that it is positioned centrally within the volume of the inner cone and separated from the fan and ion dispensers. In that way, the entire circumference of the rim 407 remains open such that there is no support structure interference within the gap 105 formed between the top 103 and the rim 407 of the cowling. By keeping the beams within the inner volume of the inner cone 406, uniform airflow is created about the entire circumference of the cowling at the exhaust gap 105 which in turn provides for more uniform dispersal of ions in a 365 degree exhaust of air from the dispersing apparatus.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A dispersing apparatus comprising:

an ion generator having an ion depositor;

a fan;

a cowling;

a top separated from the cowling by a top gap;

a base separated from the cowling by a base gap and comprising a cavity;

a controller;

the cowling comprising an outer shell and an inverted inner cone having a rim and mouth connected by a tapering cone wall, the rim of the inner cone being connected to the outer shell such that the inner cone extends into an inner cavity defined by the outer shell;

the ion depositor being positioned within the inner cone such that ions generated by the ion generator are deposited directly into the inner cone.

2. The dispersing apparatus of claim 1 wherein the fan is positioned at the mouth of the inner cone, below the ion depositor, and configured to, upon receipt of a signal from the controller, draw air into the inner cavity at the base of the outer shell and into the fan and exhaust air out of the fan past the ion depositor and through the top gap.

3. The dispersing apparatus of claim 2 wherein the top includes a conical portion that extends into a cavity defined by the inner cone.

4. The dispersing apparatus of claim 2 wherein the base includes a conical portion that extends into the inner cavity defined by the outer shell.

5. The dispersing apparatus of claim 4 wherein the fan is supported by a leg and separated from the base by the leg.

6. The dispersing apparatus of claim 1 wherein the fan is centrally positioned within the cavity defined by the outer shell.

7. The dispersing apparatus of claim 1 wherein the top gap is formed circumferentially around the rim of the inner cone, and the base gap is formed circumferentially around the bottom of the cowling and between the base and the cowling such that the top gap and base gap are each entirely open.

8. The dispersing apparatus of claim 1 wherein the ion depositor is positioned between 1-3 inches, vertically, from the fan.

9. The dispersing apparatus of claim 8 wherein the ion depositor is positioned 0.5 inches or less, horizontally, from the fan.

10. The dispersing apparatus of claim 1 wherein the controller is housed with the cavity of the base.

11. The dispersing apparatus of claim 1 wherein the top, cowling and base are symmetrical about a vertically oriented plane formed on a central vertical axis of the apparatus.

12. The dispersing apparatus of claim 1 wherein the base gap is larger than the top gap.

* * * * *